US006239088B1

(12) United States Patent
George et al.

(10) Patent No.: US 6,239,088 B1
(45) Date of Patent: May 29, 2001

(54) NONIRRITATING CLEANSING COMPOSITION

(75) Inventors: Liliana George, Centerport; Andrew J. Bevacqua, E. Setauket; Daniela Toma; Saul Miklean, both of Floral Park, all of NY (US)

(73) Assignee: Color Access, Inc., Melville, NY (US)

(*) Notice: Subject to any disclaimer, the term of this patent is extended or adjusted under 35 U.S.C. 154(b) by 0 days.

(21) Appl. No.: 09/273,061

(22) Filed: Mar. 19, 1999

(51) Int. Cl.⁷ .............................. C11D 1/66; C11D 3/22; C11D 3/26; C11D 3/04
(52) U.S. Cl. .................... 510/131; 510/136; 510/137; 510/151; 510/153; 510/158; 510/159; 510/382; 510/383; 510/470; 510/495
(58) Field of Search ...................... 510/131, 136, 510/137, 151, 153, 158, 159, 382, 383, 470, 495

(56) References Cited

U.S. PATENT DOCUMENTS

| | | | |
|---|---|---|---|
| 4,042,576 | 8/1977 | Eustache | 260/112.12 |
| 4,323,468 * | 4/1982 | Grollier et al. | 252/174.17 |
| 4,715,982 * | 12/1987 | Zabatto et al. | 252/174.17 |
| 4,963,535 * | 10/1990 | Sebag et al. | 514/54 |
| 4,968,450 * | 11/1990 | Kamegai et al. | 252/545 |
| 5,041,236 * | 8/1991 | Carpenter et al. | 252/174.12 |
| 5,165,917 * | 11/1992 | Zabatto et al. | 424/70 |
| 5,374,541 | 12/1994 | Wong et al. | 435/74 |
| 5,518,647 * | 5/1996 | Zocchi | 252/174.17 |
| 5,527,488 * | 6/1996 | Groh | 252/170 |
| 5,741,765 * | 4/1998 | Leach | 510/130 |
| 5,741,766 * | 4/1998 | Marion et al. | 510/130 |
| 5,753,631 | 5/1998 | Paulson et al. | |
| 5,977,037 * | 11/1999 | Giret et al. | 510/122 |

FOREIGN PATENT DOCUMENTS

| | | |
|---|---|---|
| 0887070 * | 12/1998 | (EP) . |
| 2 325 329 | 5/1977 | (FR) . |
| 01274247 | 2/1995 | (IT) . |
| 11-63110 | 6/1989 | (JP) . |
| 80-27181 | 1/1996 | (JP) . |
| 88053 | 7/1984 | (RO) . |
| 88054 | 7/1984 | (RO) . |
| WO 9606048 | 2/1996 | (WO) . |

OTHER PUBLICATIONS

Leon M. Prince, "HLB Emulsifier Selection System", Chapter 4, The Chemistry and Manufacture of Cosmetics, vol. III, 2nd Edition, (Continental Press, Orlando, 1975), pp. 25–37.
Peter J. Frosch and Albert M. Kligman, "The Chamber–Scarification Test for Irritancy", Contact Dermatitis 2: 314–324, 1976.
Ralph A. Kelly and Thomas W. Smith, "Pharmacological Treatment of Heart Failure", Chapter 34, pp. 809–838 and (title page), The Pharmacological Basis of Therapeutics, Ninth Edition, Joel G. Hardman and Lee E. Limbird, Editors–in–Chief, Publisher: McGraw–Hill, New York, 1996.

* cited by examiner

Primary Examiner—Gregory Delcotto
(74) Attorney, Agent, or Firm—Kenyon & Kenyon

(57) ABSTRACT

The present invention relates to a cleansing composition based on the composition of lachrymal fluid. The cleansing composition comprises an ionic aqueous base containing one or more electrolytes, a basic protein or amino acid, and optionally, a mucomimetic compound and a lysozyme. The cleansing composition is gentle to both skin and eyes, and is highly effective in removing even transfer-resistant makeup.

27 Claims, No Drawings under # US 6,239,088 B1

NONIRRITATING CLEANSING COMPOSITION

FIELD OF THE INVENTION

The present invention relates to cleansing compositions. More specifically, the invention relates to cleansing compositions which are mild and gentle to the skin and eyes.

BACKGROUND OF THE INVENTION

One of the most difficult problems for the cosmetic user is the effective removal of her makeup. As the demand for long-wearing makeup has increased, the task has become even more difficult. Traditional water-based makeup removers rely in large part on a fairly high concentration of surfactants to aid in the cleansing function. Unfortunately, such surfactants, while effective in removing makeup and other soil from the skin, can be very drying; they are also often very irritating to the eyes, and therefore, unsuitable for use in this area. Oil-based makeup remover is generally milder and very effective in removing mascara, lipstick and other cosmetics containing high levels of oil; however, these products can leave an unpleasant oily residue on the skin, leaving the user with a less than clean feeling. Thus, the ideal makeup remover, which is both mild, effective, and non-greasy, is still a very much sought-after commodity.

Any woman who has ever sobbed through a sad movie knows that nature in fact provides a very effective, if unintended, remover for makeup: lachrymal fluid. There are few women who have not experienced the inconvenience, if not embarrassment, of rivulets of mascara running down her cheeks after a good cry. The present inventors have now found a way to turn the power of tears to a more useful purpose, with the intended result of thoroughly and gently removing makeup or other soil and dirt from the skin.

SUMMARY OF THE INVENTION

The present invention relates to a skin-cleansing composition that in composition mimics lachrymal fluid, or tears. In one embodiment, the composition comprises an ionic aqueous base containing electrolyte components within the range of normal physiological fluids; in particular, the composition comprises physiological amounts of at least one, preferably at least two, and more preferably at least three, electrolytes selected from the group consisting of bicarbonate, chloride, sodium and potassium ions, in combination with a basic protein or amino acid component in amounts sufficient to buffer the composition to a pH of about 7.0–7.4, and in a preferred embodiment, the composition also comprises cleansing-effective amounts of a sialic acid compound and a lysozyme. In another embodiment, the composition comprises a cleansing effective amount of sialic acid with or without a lysozyme in an aqueous base, with or without the electrolyte and basic protein or amino acid components. The compositions of the invention are useful in a method for cleansing the skin and hair, and also, in a more specific embodiment, in a method for removing makeup from the lashes and face.

DETAILED DESCRIPTION OF THE INVENTION

The composition of human lachrymal fluid is well-known, and has components that can be divided into two main categories: structural and active. The structural components are primarily lipidic, mucinic, and aqueous, whereas the active components comprise nutrients and antimicrobial enzymes. The composition of natural tears has been previously mimicked to some extent in "artificial tears", which are recommended for use by individuals suffering from dry eyes; these products attempt to mimic the functional characteristics of the natural tear composition, while not necessarily mimicking the chemical identity. See, for example, J. Murube et al.,"Classification of Artificial Tears", in *Lacrimal Gland, Tear Film, and Dry Eye Syndromes* 2, Sullivan et al., eds., Plenum Press, 1998, pp. 693–704.

The compositions and methods of the invention are unique, in that it has not previously been suggested to employ a lachrymal fluid-like composition to cleanse the skin or hair. Unlike artificial tears, however, the cleanser of the present invention affirmatively attempts to directly mimic, to the extent possible, the actual composition of natural tears. Surprisingly, a cleansing composition mimicking the composition of lachrymal fluid provides a very effective cleansing properties, and is even useful in the difficult task of removing makeup. The compositions of the invention are also quite gentle, causing substantially no greater level of irritation to the skin than would the user's own tears.

A first component of the composition is an ionic aqueous base. The base of the composition contains physiologically acceptable levels of at least one of sodium, potassium, bicarbonate and chloride ions, and preferably a combination of two or more of these. Physiological levels of these electrolytes varies over a fairly wide range in physiological fluids, and any physiologically acceptable amount of the ions can be employed (see for example, The Pharmacological Basis of Therapeutics, Hardman et al., eds., Ninth Edition, Chapter 34, the contents of which are incorporated herein by reference). In a preferred embodiment, however, the electrolytic concentration approximates that of the lachrymal fluid, which contains about 142 meq/l sodium ions, 3–6 meq/l potassium ions, 115 meq/l chloride ions, and 5–25 meq/l bicarbonate. Preferably, ionic concentrations for each individual electrolyte will be less than about 1% by weight, more preferably about 0.5% by weight or less. In particular, in the composition, the amount of sodium ions to be used is typically, in weight percent, between 0.1% to about 0.5%, preferably about 0.2 to about 0.4%. Potassium is present in an amount of about 0.002–0.2%, preferably about 0.004–0.1%. Chloride ions are preferably used in an amount of about 0.1% to about 0.5% preferably about 0.2% to about 0.4%. Bicarbonate ions should normally be used in an amount of about .005% to about 0.3%, more preferably about 0.01 to about 0.15%. These ions can be provided in the formulation in any cosmetically acceptable form, but will normally be added in the form of sodium chloride, potassium chloride, and sodium or potassium bicarbonate, although magnesium chloride, calcium chloride, zinc chloride, sodium phosphate, or any other cosmetically acceptable material can be used.

A second component is one intended to mimic the mucinic properties(i.e., mucomimetic) of the natural tear fluid. In order for a component to perform the function of the natural mucin, it should be water soluble, confer good oncotic pressure to the fluid, and have some surfactant properties. This component is the primary surfactant of the composition and can be a naturally occurring mucopolysaccharide, mucoprotein,or mucolipid, or a surfactant effective portion thereof. Mucopolysaccharides, mucoproteins and mucolipids are obtainable commercially. Any of these materials can be used, but the preferred mucopolysaccharides, mucoproteins or mucolipids are those that contain a sialic acid component. If mucopolysaccharides are used, they are preferably present in an amount of from about 0.01 to about 10%, more preferably 0.1 to about 2% by weight of the composition.

As an alternative to the use of a whole mucopolysaccharide, it is also possible to employ a sialic acid-containing portion thereof or a sialic acid per se. A sialic acid can itself provide the necessary mucomimetic properties to the formulation. This component, which also occurs naturally in lachrymal fluid, provides a substantial increase in the cleansing properties of the composition, as they can reduce the surface tension of water. Sialic acids (nonulosaminic acids) are a family of amino sugars that are N- and O-substituted derivatives of neuraminic acid. They exist naturally, and regularly, as components of all types of mucoproteins, mucopolysaccharides, and some mucolipids. N-acetylneuraminic acid is the most common of the sialic acids and is an important component of lachrymal fluid.

Sialic acid is available from a broad range of sources, for example, by isolation from sialic acid-associated proteins, poly- and oligosaccharides, and lipids contained in eggs, milk, and mammalian submandibular glands (FR 2325329; US 40425761; JP 08-027181), and is also available commercially from Sigma. It has been reported to have a variety of uses. For example, JP 01-163110 suggests use of sialic acid, and sialic acid-associated compounds, as a skin conditioner having anti-aging properties. It is also stated as having anti-inflammatory activity (R. Matsuda, Abstract, 1st Scient. Conf. of Asian Soc. of Cosmet.Scientists, 1993). Thus, sialic acid has been suggested as a component of certain types of cosmetic compositions. It has not, however, been recognized for its cleansing properties, and cleansing compositions containing sialic acid have not been previously disclosed. The compositions of the present invention contain from about 0.01 to about 1% by weight of sialic acid, preferably about 0.05 to about .1%. Sialic acid per se may be used as the "surfactant effective portion" of the mucopolysaccharide component of the composition, and may be used alone or in combination with a mucopolysaccharide, mucoprotein or mucolipid; however, the sialic acid may also be present as an integral part of protein, lipid or saccharide complex, or in the form of a synthetic derivative, such as are described, for example, in U.S. Pat. Nos. 5,374,541 and 5,753,631. The amounts of sialic acid referred to above are with respect to substantially pure sialic acid; however, as used throughout the specification and claims,"sialic acid compound" refers not only to sialic acid per se, but also to sialic acid-containing materials, such as sialic acid containing proteins, or plant or animal extracts containing same. It is within the ability of the skilled artisan to determine the amount of sialic acid-containing material needed to provide the recommended quantities of sialic acid in the composition. As the foregoing discussion makes clear, it will thus be understood that the mucomimetic component of the composition may be a mucopolysaccharide, mucoprotein, or mucolipid containing a sialic acid portion, a mucopolysaccharide, mucoprotein or mucolipid, combined with a sialic acid compound, a natural extract containing a sialic acid component, a sialic acid compound alone, or any combination of these.

An additional component of the aqueous base will be a basic protein or basic amino acid. An important aspect of the presence of the basic protein or amino acid is to buffer what is a relatively acidic solution to a nearly neutral pH. The amount used will vary depending on the other components of the composition, but it will be an amount sufficient to bring the final pH of the formulation to into a range of from about 6 to about 8, preferably about 6.5 to about 7.5, more preferably about 7.0 to about 7.5. Basic amino acids include lysine, histidine, and arginine, or derivatives thereof, such as the arginine derivatives that inhibit NO synthase, e.g., L-NAME, ADMA, and canavanine, or ornithine hydroxylysine, and the like. As an alternative, or in addition to the use of a basic amino acid, a basic peptide or protein, i.e., one having a high proportion of basic residues, can also be used. Examples of useful basic proteins include polylysine and histidine-rich proteins(HRP). The use of these basic biological materials permits the use of smaller amounts of harsher buffering agents such as NaOH.

The aqueous base of the composition can be water or a cosmetically acceptable aqueous solutions or extracts, such as a floral water, or structured or clustered water. The latter, also known as I (acid) and S (basic) water, is particularly preferred. RO 88053 describes a method for producing basic (S-type) water, and RO 88054 discloses a method for making acid (I-type) water. Improvements in making either of these types of water are further described in WO 9606048. The use of these waters as all or a portion of the aqueous base provides certain advantages, among them the enhanced moisturization properties conferred by S water, and the enhanced activity of other components of a formulation when combined with a combination of I and S water. The waters themselves also provide a convenient source of the needed electrolytes.

In a particularly preferred embodiment, the aqueous base comprises an active component in the form of a cleansing-effective amount of the enzyme lysozyme. The latter, also known as muramidase or N-acetylmuramyl hydrolase, is a mucolytic enzyme present in a number of different secretions and tissues, such as nasal mucus, blood serum, saliva, and, like sialic acid, in tears. It is commonly isolated from egg white, but the human form can also be produced recombinantly. Lysozyme has long been known to have antimicrobial properties, and has also been reported as having antiinflammatory activity (IT 01274247). It has not, however, been known to be useful as a cleanser. In the compositions of the invention, effective amounts of lysozyme may vary depending on the source of the lysozyme. Some are more potent than others, with chicken lysozyme being less active than human lysozyme. However, for convenience of ready supply, chicken lysozyme will often be used; when used, it is present in an amount of about 0.001 to about 1%, preferably about 0.005 to about 0.5%, more preferably about 0.01 to about 0.1%, by weight of the total composition. However, it will be apparent that these amounts can be varied accordingly for less potent or more potent species of lysozyme. The presence of lysozyme in the composition also provides an advantage other than cleansing: its antimicrobial activity permits the use of very little or no preservative in the formulation.

The components described above provide a very thorough cleansing activity to the composition, and do not require any additional components to achieve this end. However, it will frequently be desirable to provide certain additional components to optimize the performance of the composition. One example of such an additional component is one or more sugars. The sugar component can be selected from monosaccharides, disaccharides, oligosaccharides and polysaccharides, or polyols obtained by the reduction of sugars, such as sorbitol, mannitol, or dulcitol. Particularly preferred sugars are sucrose or trehalose. If used, the amount of sugar component will be about 0.01 to about 10%, preferably about 0.1 to about 5%, more preferably about 0.1 to about 1%. Sugar is a naturally occurring component of lachrymal fluid, but provides an additional advantage in that it acts as an anti irritant. Certain sugars, such as the polyols, and particularly sorbitol, may also assist in solubilizing and lifting dirt from the skin during the cleansing process.

The active components of the composition as described above are water-soluble, and in formulation are combined in the aqueous component of the product. The composition can be completely aqueous or the aqueous component can also be used in any water-based vehicle, such as a gel, lotion, dispersion, or spray. It is, however, preferred that the composition contain component that mimics the lipidic component of natural tears. Thus, a preferred form for use of the compositions is an oil and water emulsion, the presence of oil assisting in suspending and removing hydrophobic soil from the skin. More preferably, the emulsion is an oil-in-water emulsion. The oil component may be any pharmaceutically or cosmetically acceptable material which is substantially insoluble in water. These materials can be found for example in the CTFA International Dictionary of Cosmetic Ingredients as well as the U.S. Pharmacopoeia or equivalent sources. The oil phase may be any cosmetically or pharmaceutically acceptable oil, such an oil being defined for the present purpose as any pharmaceutically or cosmetically acceptable material which is substantially insoluble in water. The oils may be volatile or non-volatile, or a mixture of both. For example, suitable volatile oils include, but are not limited to, both cyclic and linear silicones, such as cyclomethicone, octamethylcyclotetrasiloxane, and decamethylcyclopentasiloxane; or straight or branched chain hydrocarbons having from 8–20 carbon atoms, such as decane, dodecane, tridecane, tetradecane, and C8–20 isoparaffins.

Non-volatile oils include, but are not limited to, vegetable oils, such as coconut oil, jojoba oil, corn oil, sunflower oil, palm oil, soybean oil; esters, such as C12–15 alkyl benzoate; carboxylic acid esters such as isostearyl neopentanoate, cetyl octanoate, cetyl ricinoleate, octyl palmitate, dioctyl malate, coco-dicaprylate/caprate, decyl isostearate, myristyl myristate; fatty alcohols, such as octyldodecanol or stearyl alcohol; animal oils such as lanolin and lanolin derivatives, tallow, mink oil or cholesterol; glyceryl esters, such as glyceryl monostearate, glyceryl dioleate, glyceryl distearate, glyceryl linoleate, glyceryl myristate; non-volatile silicones, such as dimethicone, dimethiconol, dimethicone copolyol, phenyl trimethicone, methicone, simethicone; and nonvolatile hydrocarbons, such as isoparaffins, squalane, or petrolatum. The preferred oil components are non-volatile oils, particularly esters. In a preferred embodiment, the oil component of an oil-in-water emulsion is present in an amount of about 1 to about 30%, more preferably about 5 to about 20% by weight of the total composition.

When the composition takes the form of an emulsion, it is preferred that one or more emulsifiers is also employed. The preferred emulsion is an oil-in-water emulsion. For such emulsions, any high hydrophilic-lipophilic balance (HLB) emulsifier, or a combination of emulsifiers, can be employed. A useful oil-in-water emulsifier will be one having an HLB of at least 6, or a mixture of such emulsifiers with one or more water-in-oil emulsifiers(i.e., emulsifiers having an HLB of from about 2 to about 6), in which case the type and amount of each emulsifier present in the mixture is selected such that the effective HLB of the resultant oil-in-water emulsifier component is at least about 6. Techniques for combining and ascertaining the effective HLB of a mixture of emulsifiers are known; see L.M.Prince, in M.G. DeNavarre,"The Chemistry and Manufacture of Cosmetics", Volume III, Second Ed., (Continental Press, Orlando, 1975), pp. 25–37.

Suitable oil-in-water emulsifiers include, but are not limited to, sorbitol derivatives, such as sorbitan monolaurate, and polysorbate 20, polysorbate 21 or polysorbate 60; lecithin and lecithin derivatives; ethoxylated alcohols such as laureth-23, ethoxylated fatty acids such as PEG-1000 stearate, PEG-20 methyl glucose sesquistearate, PEG-80 glyceryl cocoate, PEG-20 sorbitan isostearate, and PEG-120 methyl glucose dioleate; amidoamine derivatives such as stearamidoethyl diethylamine; sulfates of alcohols, such as sodium lauryl sulfate; phosphate esters such as DEA cetyl phosphate and potassium stearyl phosphate; glyceryl esters, such as polyglyceryl-2 PEG-4 stearate and polyglyceryl-2 sesquistearate; polymeric esters, such as poloxamers 181, 184, 105, 124, 401, and 407; amido-sulfonic acid derivatives, such as sodium methyl cocoyl taurate; sulfosuccinates, such as disodium ricinoleamido MEA-sulfosuccinate, fatty acid amine salts such as TEA stearate and stearamide MEA stearate; sarcosine derivatives, such as sodium cocoyl sarcosinate, and mixtures thereof. However, in keeping with the gentle nature of the cleansing components, a very mild emulsifier is preferred. Particularly preferred are sucrose or glucose esters or their derivatives, for example, sucrose stearate, sucrose distearate, sucrose cocoate, alkyl glucoside, alkyl polyglucoside, alkyl polyglycoside, methyl gluceth 20 distearate, methyl glucoside dioleate, methyl glucoside sesquistearate, methyl glucose dioleate, methyl glucose isostearate, methyl glucose sesquistearate, stearyl glucoside, and glucose glutamate.

The compositions may also comprise additional cosmetic additives to enhance the aesthetics of the formulation. Although it is generally preferred that the composition be non-pasty, it may be desirable to include a small amount of one or more thickeners or viscosifiers, such as, for example, hectorites, gums, celluloses, waxes, alginates, carageenans, starches, silicates or fatty alcohols. The thickener, if used, will normally be present in amount of about 0.01–5%, preferably about 0.1–2%, by weight of the composition.

Although the components outlined above provide adequate cleansing activity on their own, in a preferred embodiment, the compositions also contain a small amount of secondary surfactant, to enhance the cleansing properties of the cleansing components listed above. If used, the surfactant should be selected from those which are very mild, such as protein-based surfactants, sugar-based surfactants, and amphoteric or non-ionic surfactants generally. Particularly preferred are mild carboxylic-acid based surfactants. In the case of use of such a surfactant, the carboxyl moiety of the acid can react with and neutralize basic amino acid(s) used in the formulation, thereby reducing further the possibility of irritation. Examples of such surfactants include behenic acid, coconut fatty acids, caprylic/capric fatty acid, capric acid, soybean fatty acid, tallow fatty acid, olive oil fatty acids, or ethoxylated versions of any of these. Less preferred, but also possible, are surfactants such as polyvinyl alcohol, PVP, poloxamers, polyacrylic acid, polyethylene glycols, polyoxyethylene/polyoxypropylene glycols, polysorbates, tyloxapol, lecithin, alginates, xanthans, or macrogels. Preferably, the surfactant is used in an amount greater than zero, up to about 2%, and more preferably is used in an amount of about 0.1 to about 1% by weight.

The cleansing compositions can also contain small quantities of cosmetically acceptable preservatives, such as parabens. These will preferably be used in an amount of less than about 1%, if used at all, as these are often perceived as irritating. When lysozyme, which itself has antimicrobial activity, is present, the need for traditional preservatives is reduced or eliminated. It may be useful to provide the formulation with a small quantity, e.g., up to 5 ppm, of colloidal silver to enhance the antimicrobial properties of the formulation.

The compositions of the invention are used as would be any other cleanser or makeup remover. As an example, for use in general cleansing, the composition can be applied as a facial cleanser to the face in the morning and the evening, rubbed gently, either by hand or with the use of a scrubbing implement, and rinsed off with water. The composition can also be used as a body cleanser in the same manner. In a particularly preferred cleansing use, the composition is used to remove makeup, even for long-wearing or transfer-resistant makeup. In this application, the composition is applied wherever makeup has been used, e.g., either lashes or skin, rubbed gently as noted above, and rinsed off with water, or removed with a tissue or wash cloth with a subsequent rinsing with water. The compositions of the invention are surprisingly mild, with an irritation index comparable to a saline solution, and can therefore be used regularly without concern for irritation or drying of the skin.

The invention is further illustrated by the following non-limiting examples.

EXAMPLES

Example I

A-composition of the invention is prepared as follows:

| Material | Weight % |
|---|---|
| Phase I | |
| Water (I and S) | QS |
| Sodium chloride | 0.250 |
| sucrose | 0.500 |
| Disodium EDTA | 0.050 |
| sialic acid (SIGMA) | 0.100 |
| cocoeth-7 carboxylic acid | 1.000 |
| sodium bicarbonate | 0.003 |
| Phase II | |
| L-arginine | 0.100 |
| Phase III | |
| Methyl glucose sesguistearate | 2.000 |
| glyceryl monostearate | 2.000 |
| stearyl alcohol | 1.750 |
| $C_{12-15}$ alkyl benzoate | 10.000 |
| Phase IV | |
| Colloidal (MAG 500) silver | .100 |
| Phase V | |
| Water | 20.000 |
| Lysozyme (SIGMA) | 0.100 |

Phase I ingredients are combined at 70° C., and mixed to homogeneity. Phase II is added cold to the Phase I ingredients until the pH reaches about 7.7. Phase III ingredients are mixed with the Phase I and II ingredients at 70° C. Phase IV is then added to the mixture at 30° C. The Phase IV ingredients are premixed, and added to the mixture at 30° C., bringing the pH to about 6.84.

Example II

A composition of the invention similar to the one described above, but containing no lysozyme, 0.02% BTC (50% solution), 0.1 NaOH (30% solution) (formula A), as well as a corresponding composition without sialic acid, sodium chloride and sodium hydroxide(Formula B), are tested on ten panelists to determine the compositions potential to cause irritation in the chamber scarification test of Kligman (Frosch and Kligman, Contact Dermatitis 2: 314–324, 1976).

Results are scored in accordance with the amount of irritation observed, on a range from 0.0–4.0, with 0.0–0.49 being very low irritation, 0.5–1.49 being low; 1.5–2.49 being moderate; and 2.5–4.0 being high. At 24 hours, formulas A and B score at 0.75 and 0.7, respectively; at 48 hours, 1.15 and 1.2, respectively; and at 72 hours, 1.3 and 1.2 respectively. At the same time points, saline solution scores at 0.65, 0.65 and 0.55. These results indicate that the compositions of the invention are gentle and non-irritating, being in the same irritancy range as saline solution.

The same formula is also subjected to in vitro ocular testing to evaluate eye irritancy potential, and similarly scores low on the irritation scale.

What is claimed is:
1. A cleansing composition comprising an ionic aqueous base containing
   (a) at least one electrolyte component selected from the group consisting of sodium chloride, potassium chloride, sodium bicarbonate, potassium bicarbonate, magnesium chloride, calcium chloride, zinc chloride and mixtures thereof, each ion being present in an amount within the range of normal physiological fluids; and
   (b) a basic protein or amino acid component in amounts sufficient to buffer the composition to a pH of about 6 to about 8; and
   (c) 0.01% to 10% by weight of a primary surfactant comprising a nucomimetic selected from the group consisting of a mucopolysaccharide containing a sialic acid component, a mucoprotein containing a sialic acid component, a mucolipid containing a sialic acid component, a sialic acid component, a plant or animal extract containing a sialic acid component, and mixtures thereof.

2. The composition of claim 1 which comprises at least two electrolyte components selected from the group consisting of cosmetically acceptable sources of chloride, sodium, potassium and bicarbonate ions.

3. The composition of claim 1 in which component (b) is a basic amino acid.

4. The composition of claim 1 comprises at least two electrolyte components selected from the group consisting of cosmetically acceptable sources of chloride, sodium, potassium and bicarbonate ions, and a basic amino acid.

5. The composition of claim 1 which also comprises a cleansing effective amount of a lysozyme.

6. The composition of claim 1 which also comprises a secondary surfactant.

7. The composition of claim 6 in which the surfactant is present in an amount of no more than 2%.

8. The composition of claim 1 which is an oil and water emulsion.

9. A cleansing composition comprising an ionic aqueous base containing
   (a) at least two electrolyte components selected from the group consisting of sodium chloride, potassium chloride, sodium bicarbonate, potassium bicarbonate, magnesium chloride, calcium chloride, zinc chloride and mixtures thereof, each in an amount within the range of normal physiological fluids;

(b) a basic protein or amino acid component in amounts sufficient to buffer the composition to a pH of about 6 to about 8; and (c) 0.01% to 1% by weight of a primary surfactant which is a sialic acid compound.

10. The composition of claim 9 which also comprises a cleansing effective amount of a lysozyme.

11. The composition of claim 9 in which component (b) is an amino acid.

12. The composition of claim 9 in which component (b) is arginine.

13. The composition of claim 9 which also comprises a secondary surfactant in an amount greater than zero and no greater than about 2%.

14. The composition of claim 13 in which the surfactant is selected from the group consisting of protein-containing surfactants, sugar-containing surfactants, amphoteric surfactants, and carboxylic acid-containing surfactants.

15. The composition of claim 14 in which the surfactant is a carboxylic acid-containing surfactant.

16. The composition of claim 9 which is a oil and water emulsion.

17. The composition of claim 16 which is an oil-in-water emulsion comprising an emulsifier having an HLB of 6 or greater.

18. The composition of claim 17 in which the emulsifier is selected from the group consisting of sucrose and glucose esters.

19. The composition of claim 9 which is an oil-in water emulsion comprising (a) at least two electrolytes;

(b) arginine in an amount sufficient to buffer the composition to a pH of about 6 to about 8;

(c) a sialic acid compound;

(d) a sucrose or glucose ester emulsifier; and (e) a carboxylic acid-containing surfactant, the surfactant present in an amount of no more than about 2% by weight of the composition.

20. The composition of claim 19 in which the aqueous base comprises I water, S water, or a combination thereof.

21. The composition of claim 19 which has a pH of about 6.5 to about 7.5.

22. The composition of claim 19 in which the emulsifier comprises methyl glucose sesquistearate.

23. The composition of claim 19 in which the surfactant comprises a fatty acid, or an ethoxylated form thereof.

24. The composition of claim 19 which also comprises a cleansing effective amount of a lysozyme.

25. A method for cleansing the skin which comprises applying to the skin a cleansing composition according to claim 1.

26. A method for cleansing the skin which comprises applying to the skin a cleansing composition according to claim 9.

27. A method for cleansing the skin which comprises applying to the skin a cleansing composition according to claim 19.

* * * * *